United States Patent [19]

Sherinski

[11] 4,227,083
[45] Oct. 7, 1980

[54] APPARATUS FOR INFRARED LASER SPECTROSCOPY OF ROOM TEMPERATURE VULCANIZABLE SILICONE COMPOSITIONS

[75] Inventor: Lawrence R. Sherinski, Ballston Lake, N.Y.

[73] Assignee: General Electric Company, Waterford, N.Y.

[21] Appl. No.: 8,818

[22] Filed: Feb. 2, 1979

[51] Int. Cl.² .............................................. G01J 1/00
[52] U.S. Cl. .................................... 250/343; 250/341
[58] Field of Search ............... 250/338, 340, 343, 341

[56] References Cited

U.S. PATENT DOCUMENTS

| | | | |
|---|---|---|---|
| 3,856,406 | 12/1974 | Noble et al. | 250/343 |
| 3,911,276 | 7/1975 | Bell | 250/343 |
| 3,987,304 | 10/1976 | Kreuzer | 250/343 |
| 4,068,125 | 1/1978 | Bell | 250/340 |

Primary Examiner—Davis L. Willis
Assistant Examiner—Janice A. Howell
Attorney, Agent, or Firm—Michael J. Doyle; John L. Young; E. Philip Koltos

[57] ABSTRACT

A method and apparatus for the continuous and automatic analysis of a process stream is disclosed. A tunable laser capable of delivering high intensity infrared radiation at a predetermined wavelength is used to monitor the crosslinker content of a room temperature vulcanizable composition (RTV) during its manufacture. Methyltriacetoxysilane is a crosslinking component in acetoxy system RTV's and contains a carbonyl group which absorb infrared radiation very strongly at certain predetermined frequencies. Determination of the amount of infrared absorption by the crosslinker is directly related to the determination of the crosslinker content in a process stream of RTV.

17 Claims, 2 Drawing Figures

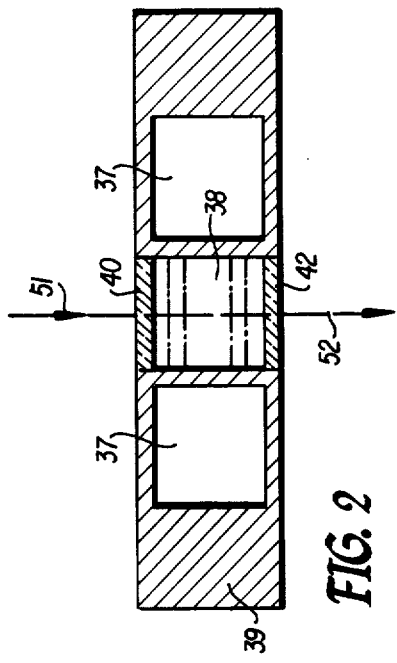
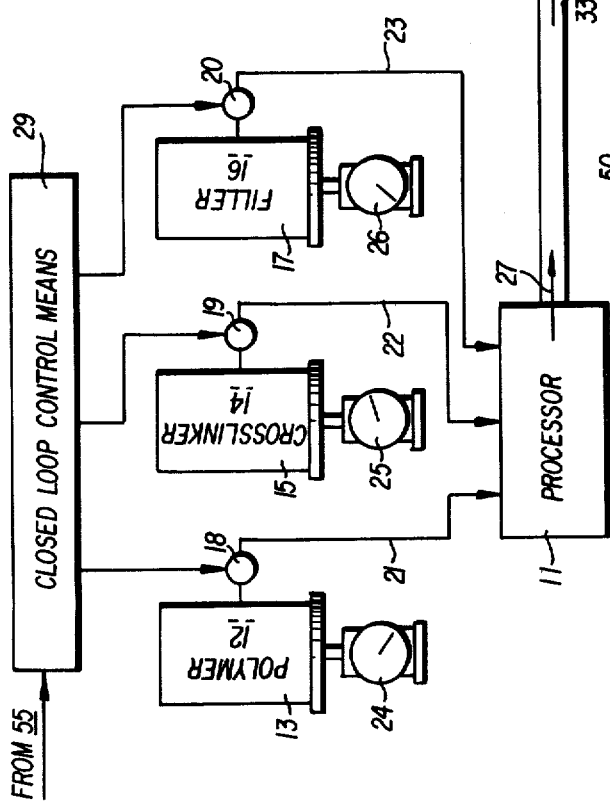
FIG. 2
FIG. 1

APPARATUS FOR INFRARED LASER SPECTROSCOPY OF ROOM TEMPERATURE VULCANIZABLE SILICONE COMPOSITIONS

BACKGROUND OF THE INVENTION

The present invention relates to the analysis of a process stream of room temperature vulcanizable (RTV) silicone material to determine the content of a crosslinking agent therein through the use of continuous and automatic infrared laser spectroscopy.

Room temperature vulcanizable materials (RTV's) are silicone rubber compositions typically made up of a silanol-terminated linear diorganopolysiloxane polymer, one or more crosslinking agents, a catalyst, and a filler or other optional ingredients. In an acetoxy system of one-package or one-component RTV's for example, one of the primary crosslinkers is methyltriacetoxysilane. It is desirable to know the relative concentration of the crosslinker in the RTV composition because the amount of crosslinker directly affects the properties of the final product, i.e., the rate of cure and the viscosity of the cured product are dependent upon crosslinker content.

These compositions are prepared and stored in an anhydrous state and will cure to a silicone elastomer in the presence of atmospheric moisture. These products are utilized for a variety of purposes as, for example, formed-in-place gaskets and are widely used in many sealant applications. Silicone rubber compositions are quite adhesive to most substrates and exhibit outstanding resistance to ozone and ultraviolet rays as well as adverse weather conditions. Such compositions also have desirable tensile strength and modulus in many applications as well as being capable of performing effectively from very low temperatures such as $-60°$ F. to excessively high temperatures such as $300°$ F. or more. Another advantage of one-component RTV compositions is their ability to be utilized directly at a job site without prior mixing.

RTV silicones are relatively viscous materials which are difficult to mix thoroughly. Typically, an RTV could exhibit a viscosity during its manufacture from about 75,000 centipoise to about 600,000 centipoise or more in its uncured state. It is therefore important that the crosslinker concentration be readily determined in order to provide a consistent final product.

Analysis methods and apparatus heretofore employed in the art were susceptible to several problems overcome by the present invention. For example, the crosslinker concentration could be determined by standard laboratory titration techniques, but such techniques are inherently non-continuous and must ordinarily be carried out by a skilled technician.

The methyltriacetoxysilane crosslinker mentioned above contains a carbonyl group which can be identified by titration. However, titration techniques also determine all other carbonyl-containing species in a given sample whereas the present invention provides a method and apparatus for selectively determining the active or effective crosslinker content in a given sample. The effective amount of crosslinker can be less than the total amount because of side reactions which could occur. For example, when methyltriacetoxysilane is used as a crosslinker, acetic acid is a volatile byproduct of the crosslinking reaction and a certain amount of this acid can be formed during manufacture, especially when conditions are not absolutely anhydrous. The method of the present invention can selectively determine the content of a particular constituent in a process stream such as the effective amount of catalyst while ignoring the presense of an interferring material such as acetic acid.

The carbonyl group in the methyltriacetoxysilane crosslinker absorb infrared radiation strongly at certain frequencies. An example of infrared spectroscopy utilizing a laser absorption spectrometer is disclosed in U.S. Pat. No. 3,856,406—Noble, issued Dec. 24, 1974, and assigned to the same assignee as the present invention, wherein an unknown gas sample is analyzed in an air pollution monitoring technique. U.S. Pat. No. 3,987,304—Kreuzer, issued Oct. 18, 1976, discloses infrared laser absorption spectroscopy of a gaseous stream such as the effluent stream of a retention time chromatograph. The Kreuzer apparatus utilizes an optoacoustic detecting means but does not teach analysis of an RTV process stream.

While lasers have heretofore been utilized for infrared absorption spectroscopy, materials which lend themselves more readily to such techniques are ordinarily analyzed. Until the present invention, it has not been possible to continuously analyze a room temperature vulcanizable silicone composition because of properties inherent to these materials.

One property of RTV which presents problems in the analysis of these compositions is the high viscosity of the material. The material also exhibits a tackiness that makes it difficult to obtain uniformly consistent samples. These properties of RTV make it nearly impossible to obtain on a continuous basis uniform thin samples required by standard methods of infrared analysis when it is diluted with a solvent which is different.

Accordingly, in order to continuously analyze an RTV process stream at a rate which substantially corresponds to the rate at which the material is being manufactured and moving in the stream, it is necessary to utilize a relatively much thicker sample of RTV. While a thicker sample overcomes the aforementioned problems concerning flow rate, it compounds a problem associated with infrared spectroscopy. Specifically, thick samples of RTV materials are relatively opaque with respect to infrared radiation at the frequencies which are useful for analysis, i.e., most of such radiation is absorbed by the material and little is left to pass through the sample for analytical purposes.

It has been suggested that conventional attenuated total reflectance laser spectrometers can be used to overcome the above-mentioned characteristic opacity of RTV materials; however, such an approach does not satisfy the requirement for continuous analysis. Nor do standard methods of infrared spectroscopy which utilize incandescent sources of infrared radiation or lasers with an intensity of about one milliwatt satisfy such requirements. Ordinarily, infrared spectroscopy is used to analyze materials such as a gas or a liquid which is relatively transparent to infrared. In such applications most of the infrared passes through the sample and only a small fraction thereof is absorbed by it. The small amount that is absorbed can be detected and analyzed. For RTV materials, however, over 98% of the infrared radiation is absorbed by the sample. In light of this, the present invention employs high intensity lasers and sensitive detecting means in order to determine the characteristic absorption of a constituent in the process stream under consideration.

One object of the present invention is to provide a novel method and apparatus for continuous and automatic analysis of a flowing RTV process stream for the content of a crosslinking agent or other constituent therein.

Another object of the present invention is to provide a novel method and apparatus employing a high intensity laser as the source of infrared radiation in order to overcome a number of problems previously encountered in the analysis of RTV.

Another object of the present invention is to provide a novel method and apparatus employing a high intensity source of radiation which obviates the need for a relatively thin sample to be analyzed, whereby analysis can be accomplished quickly and continuously.

An additional object of the present invention is to provide a new and improved apparatus which comprises a particular high intensity infrared radiation source and adapting the apparatus for effective operation in spite of the characteristic relative infrared opacity of RTV material.

Still another object of the present invention is to provide a novel method and apparatus such that the continuous analysis of an RTV composition takes place at a rate that corresponds substantially with the flow rate of the main portion of the RTV process stream from which the portion to be analyzed is taken, and does not affect the properties of the materials that have been analyzed.

These and other objects and advantages of the present invention will become better understood from a reading of the following specification and claims and consideration of the accompanying drawing.

SUMMARY OF THE INVENTION

In accordance with the above objects, there is provided by the present invention, a method and apparatus for the continuous analysis of a process stream and more particularly, a method for determining the concentration of a particular constituent in that stream. For the manufacture of a room temperature vulcanizable silicone composition (RTV), several starting materials are introduced into a processor. These materials may include a silanol-terminated diorganopolysiloxane polymer as the major constituent, a crosslinking agent such as methyltriacetoxysilane in an amount from about 2% to about 5% of the total weight, and a small amount of catalyst such as dibutyl tin dilaurate in an amount ordinarily less than 1% of the total weight. Other additives and fillers may optionally be used depending upon the properties desired in the final product. Such fillers can include silica, titanium oxide, talc, mica or zinc oxide among others.

As the silicone composition is being manufactured, a determination is made as to the approximate viscosity of the material in the process stream in order that it may flow efficiently between the infrared transparent windows provided by the sample cell.

It is then decided which constituent of the process stream is to be monitored. If the crosslinker is methyltriacetoxysilane, it is known that this material contains a carbonyl group which absorb infrared radiation at certain frequencies. A suitable absorption frequency is then selected and the source of infrared radiation such as a tunable laser is employed to operate at that frequency. Next, the operating intensity of the laser at the preselected frequency is selected so that the problem of infrared opacity is minimized. This selection is made upon consideration of the two factors which influence the infrared opacity of the material, namely, the thickness of the sample and the characteristic infrared absorption of the material at the preselected frequency.

Any constituent in the process stream which could be analyzed by conventional infrared methods could also be analyzed by the present invention. As noted above, it is useful to determine the crosslinker composition of a room temperature vulcanizable silicone composition in order to insure a uniform and consistent final product. Room temperature vulcanizable silicone compositions can contain other crosslinking materials than that mentioned above. These crosslinkers can be silanes and siloxanes which are alkoxy functional, acyloxy functional, amine functional, amide functional, and ketoximino functional silanes and siloxanes. These crosslinkers can be analyzed by the method of the present invention by selection of a suitable chracteristic infrared absorption frequency.

The invention will be more distinctly set forth hereinbelow.

BRIEF DESCRIPTION OF THE DRAWINGS

FIG. 1 is a schematic plan for an RTV manufacturing process.

FIG. 2 is a sectional view of a sample cell utilized by the present invention.

DESCRIPTION OF THE PREFERRED EMBODIMENT

FIG. 1 depicts schematically, a manufacturing process and apparatus adapted for the production of a room temperature vulcanizable silicone composition (RTV) or a similar polymeric material in accordance with the present invention. A suitable starting material 12 such, for example, as a diorganopolysiloxane polymer is contained in a vat 13. Similarly, another starting material, namely, a crosslinker composition 14, is initially contained in a vat 15. In a one-package system of acetoxy RTV's of a type with which the present invention is particularly well adapted to be used, a suitable crosslinking composition is methyltriacetoxysilane.

RTV's and other elastomeric compositions may contain a plurality of other ingredients such, for example, as a catalyst or a filler 16 which is contained in a vat 17. Each of the starting materials 12, 14 and 16 are fed, respectively, by conduits 21, 22 and 23 to a processor 11 for admixing the materials and manufacturing a final product indicated by 27 in the processor 11 and in a stream bed which can be a large conduit 28. The starting materials enter the processor 26 at a rate regulated by control means such as valves 18, 19 and 20.

The control means 18, 19 and 20 can be operated manually by a technician or automatically as a result of well-known closed loop control means 29. The starting materials in vats 13, 15 and 17 are situated in relation to balances 24, 25 and 26, respectively, to allow an operator to make gross adjustments to the rates of flow of the starting materials into the processor 11. The processor 11 works continuously and the final RTV product 27 is carried by means of the conduit 28 to a receptacle 30.

Preferably, the relative concentrations of the starting materials 12, 14 and 16 in the final product 27, should be known to an accuracy greater than that provided by a mere reading of the balances 24, 25 and 26. For example, the preferred embodiment of the present invention enables one to know with an accuracy of ±0.1% the concentration of the methyltriacetoxysilane or other crosslinker 14 in the final RTV product 27. This, in turn, enables one to predict the characteristic properties such as cure rate and viscosity of the final RTV product. The present invention affords continuous monitoring of the crosslinker content in order to insure a uniform final product.

In the presently disclosed embodiment of the invention, the continuous monitoring is accomplished through the use of a bypass sampling means 33 which diverts a portion 35 of the process stream of the final product 27 from the stream bed in conduit 28 and conveys the diverted portion of a sample detection region.

Additionally, not all of the bypassed portion of the stream is used for analytical purposes. More specifically, the stream portion 35 is divided into minor and major portions and only the minor portion 38 is continuously analyzed while the major portion 37 is directed back into the main stream at a rate which is substantially unimpeded by the apparatus of the sample cell 39. A pump 34 may be provided to adjust the flow rate of the sample to be analyzed.

Minor stream 38 passes into sample cell 39 and flows continuously between a pair of opposed parallel infrared transparent windows before exiting the sample cell. As better seen in FIG. 2, which is a cross-sectional view of sample cell 39, minor stream 39 flows continuously out of the plant of the paper between windows 40 and 42.

Major stream 37 flows in likewise manner through the sample cell 39 but is substantially unimpeded by the structure of the sample cell as compared to minor stream 38. The major stream 37 optionally returns to the main stream by means of conduit 41.

In order that the sample cell 39 will function for the purposes of this invention and in order that the RTV sample will flow continuously and efficiently through the cell, the distance between the windows 40 and 42 must be appropriately adjusted in accordance with the viscosity of the sample flowing therebetween. As an example, for the analysis of an RTV containing methyltriacetoxysilane crosslinker, which might have a viscosity of about 300,000 centipoise at 25° C. in its uncured state during manufacture, it is most preferred that the window spacing be approximately 0.022 inches apart in order that the sample flow efficiently between the windows. A relatively more viscous sample of RTV requires window spacing which is greater than that required for a less viscous sample. In one embodiment of the present invention where the polymeric composition under consideration is not particularly viscous, the infrared transparent windows 40 and 42 may be spaced approximately 0.010 inches apart. For a sample which is relatively very viscous, the window spacing can be as great as approximately 0.030 inches. In a preferred embodiment and where a relatively viscous RTV sample is being analyzed, the spacing is from approximately 0.018 inches to approximately 0.024 inches apart. A source of infrared radiation 50 is located so as to direct a beam 51 of infrared radiation through the infrared transparent windows 40 and 42 and the minor stream 38 flowing therebetween. Most of the infrared radiation in beam 51 is absorbed by the minor stream 38 but an amount which is not absorbed is represented by beam 52 which is directed to detecting means 53.

The source of infrared radiation 50 is chosen to match the sample under consideration. As noted above, if the minor stream 38 is relatively less viscous than ordinary RTV samples, which may be the case if the sample is diluted, then relatively thin samples can be utilized, i.e., the infrared transparent windows 40 and 42 can be spaced closer to each other and the sample (minor stream 38) will still flow efficiently therebetween. In such a case, the source of infrared 50 can be an incandescent lamp or a standard laser operating at an intensity of about 1 milliwatt. But as the necessity for a thicker sample due to viscosity problems increases, it also becomes necessary to utilize a more powerful laser as the source of infrared radiation 50 because a thicker sample of RTV is necessarily more opaque towards infrared than a thin sample. In one embodiment of the present invention where RTV is being analyzed for its methyltriacetoxysilane content, the laser operates at an intensity of more than ten milliwatts. The intensity may vary in usual operation from about one milliwatt to about thirty milliwatts. The intensity of the infrared source 50 is selected after determining two factors, i.e., the relative thickness of the sample 38 flowing between windows 40 and 42 (which is dependent on the viscosity of the RTV stream) and also the characteristic opacity towards infrared of the material under consideration at the preselected frequency.

RTV is relatively opaque to infrared radiation when compared to other materials which have previously been subjected to infrared analysis. It is noted that at a frequency that is useful for infrared absorption spectroscopy an RTV sample will absorb over 98% of the infrared radiation leaving a small fraction available for detection and analysis. Therefore, in a preferred mode of operation, this invention utilizes, as a source of infrared radiation 50, a laser effective for producing a beam of coherent infrared radiation 51 at an intensity which is adjustable from about one milliwatt to about thirty millwatts.

A methyltriacetoxysilane crosslinker 14 contains several a group which absorb infrared radiation strongly at known wavelengths. For example, it is known that the methyltriacetoxysilane will absorb infrared very strongly at a frequency of about 1750 cm$^{-1}$, but in the present invention it is preferred to analyze at a frequency which is off-band center. An off-band center frequency is one which still exhibits characteristic infrared absorption for the material under consideration yet the material is relatively less opaque and thus easier to analyze. Such a frequency is between 1775 and 1800 cm$^{-1}$ for the particular crosslinker methyltriacetoxysilane; however, many frequencies of infrared radiation can be used and such frequencies are selected to correspond to a characteristic absorbence frequency of the material under investigation.

For example, in another system of room temperature vulcanizable materials known as "alkoxy"RTV's, the crosslinker 14 is an alkoxy compound as distinguished from the acetoxy crosslinker utilized in the above discussion. Alkoxy compounds contain functional groups which can be effectively analyzed, monitored and controlled by the infrared spectroscopic techniques of the present invention. Indeed, many types of RTV compositions can be analyzed during their manufacture in the same manner. After a preliminary determination is made as to the viscosity of the process stream so that the sample windows can be adjusted, a suitable absorption frequency for the material to be analyzed is selected. Other types of RTV's contain crosslinking agents which contain functional groups that can be analyzed by infrared spectroscopic techniques. Each functional group will have characteristic infrared absorption frequencies and the present method and apparatus can be made to operate at these frequencies. Examples of other RTV crosslinking agents include those which are alkoxy functional, acyloxy functional, amine functional, amide functional, and ketoximino functional silanes and siloxanes.

As described above, the beam 51 of coherent infrared radiation is directed through the infrared transparent windows 40 and 42 of sample cell 39 and the minor stream 38 flowing continuously therebetween. The amount of infrared radiation that is not absorbed by the sample, is measured by a detecting means 53. The detecting means 53 can be any detector which is sufficiently sensitive to measure the amount of infrared absorption by the infrared functional groups in the crosslinker 14 contained in process stream 27 and minor stream 38. In the illustrated embodiment of this invention, detector 53, is a thermoelectric detector. Other detectors such as photodetectors can be alternatively used. The amount of absorption detected is determinitive of the content of the crosslinking agent in the RTV process stream 27 by application of standard spectroscopic techniques. Data representative of the content of the crosslinker in the cell at a given point in time is fed to a programmable computer 55 which interprets such data for a plurality of purposes. For example, in one embodiment of the present invention, the programmable computer 55 is effective for the long term storage 63 of absorption and crosslinker content data. Alternatively, the programmable computer 55 may be effective for depicting such data on a trend recorder 62 for immediate use by operators of the process.

It is most preferred that the programmable computer 55 be effective for determining whether the crosslinker 14 content of process stream 27 is either too high or too low, either of which could result in an inconsistent final product 27 entering the receptacle 30. In either situation, appropriate coupling means 58 and 59 are provided by convey information regarding crosslinker content to a closed loop control system 29 which is effective for automatically and continuously controlling the respective regulating means 18, 19 and 20 and predeterminedly controlling the flow of each of the materials 12, 14 and 16 into the processor 11.

Additionally, means are provided for continuously monitoring the flow rate of minor stream 38 through sample cell 39 between the infrared transparent windows 40 and 42. Stream 38 is directed by conduit 43 to a flow detecting means 44. The flow detecting means 44 can be, for example, a pressure transducer or as embodied in the present invention, a balance effective for detecting an incremental increase in the amount of RTV product flowing in the minor stream 38 through the sample cell 39 from conduit 43 into a receptacle 31.

The programmable computer 55 is capable of interrogating the data from the flow detecting means 44. The computer is effective for operating an alarm or indicating means 56 when the flow detecting means 44 indicates that the minor stream 38 has stopped flowing through sample cell 39. Similarly, the computer is effective for operating an alarm or indicating means 57 if the flow detecting means 44 indicates an overflow situation. In such a case the programmable computer 55 is effective for shutting down the system to avoid damage.

EXAMPLE

A room temperature vulcanizable silicone composition containing a silanol-terminated dimethylpolysiloxane, a silica filler, a dibutyl tin dilaurate catalyst and a methyltriacetoxy crosslinker was manufactured and analyzed by the present method. The RTV composition had a viscosity of about 300,000 centipoise as measured by an HBF Brookfield Viscometer at a temperature of 25° C. It was found that a window spacing of approximately 0.022 inches provided enough room for the material to flow efficiently through the sample cell. A frequency of approximately 1781 cm$^{-1}$ was selected because it corresponds to a suitable infrared absorption frequency for identifying the functional carbonyl content in the process stream which thus relates to the methyltriocetoxysilane content therein. The laser was operated at a power intensity of about 22 milliwatts in order to overcome the characteristic infrared opacity of this material at this particular frequency and sample thickness. It was found over the course of 6 hours that as the crosslinker feed rate into the process was varied and the feed rates of the other starting materials remained constant, the crosslinker content at any particular moment could be determined. The laser analyzer tested the continuously flowing sample every 6 seconds. It was determined that the methyltriacetoxysilane crosslinker content in the final product varied throughout the course of the experiment from approximately 4.5±0.1% to approximately 2.5±0.1% as the feed rate of the crosslinker was decreased.

Since the laser analyzer utilized by the present invention responds to a very narrow fraction of the total carbonyl absorption spectrum and is influenced little or not at all by other carbonyl species which may be present, it provides an accurate evaluation of the active or remaining available crosslinker contained in the sample. It is possible to install a second laser which can be tuned, for example, to a frequency corresponding to the absorption frequency of some other constituent in the process stream. Thus, it is possible to monitor the content of more than one constituent simultaneously. For instance, in the system utilizing methyltriacetoxysilane crosslinker, it has been noted above that a small amount of acetic acid will also be present as a volatile by-product; by using two lasers, both carbonyl species can be determined and any mutual interaction can be compensated by the programmable computer.

Actually, additional lasers tuned to other characteristic absorption frequencies can be used to determine those species having functional groups absorbing infrared radiation at those specific frequencies. For example, a marked infrared absorption at about 1442 cm$^{-1}$ results from the presence of aromatic rings. Thus, additives containing aromatic rings can be monitored if one of the lasers is operating at an appropriate absorption frequency.

It will be seen from the foregoing that the present invention provides a new and novel method and apparatus for controlling a manufacturing process for RTV's and more specifically for analyzing the concentration of a constituent of the material on a continuous and automatic basis utilizing high intensity laser absorption spectroscopy.

This novel process results in a uniquely uniform RTV product which has properties that exhibit a remarkable degree of consistency and ensures uniformity of performance as compared to products made by prior art processes. Additionally, the ability to produce a uniform product on a continuous and automatic basis results in a process which is more efficient than those practiced by the prior art.

What is claimed as new and desired to be secured by Letters Patent of the United States is:

1. Apparatus for determining the concentration of a constituent in a process stream, comprising:
   (a) means for bypassing a portion of said stream to a sample detection region;
   (b) means for splitting said portion of said stream into first and second parts and diverting said first part from said sample detection region;
   (c) a sample cell comprising a pair of opposed infrared transparent windows extending in parallel planes wherein the space between said windows is adjusted upon consideration of the relative viscosity of said second part of said stream;
   (d) means for diverting said second part of said stream through said sample cell between said windows and wherein the space between said windows defines the thickness of the sample stream flowing therebetween;
   (e) a laser effective for directing a beam of infrared radiation maintainable at a predetermined frequency corresponding to a selected infrared absorption frequency of the constituent in the process stream under consideration through said windows of said cell and said second part of the process stream flowing therebetween; and
   (f) means for continuously detecting the proportion of said infrared radiation at said predetermined frequency absorbed by said second part of said stream in said sample cell.

2. Apparatus as in claim 1, wherein the opposed infrared transparent windows are spaced from approximately 0.010 inches to approximately 0.030 inches.

3. Apparatus as in claims 1 or 2, wherein the laser is operative at a power intensity effective to overcome the characteristic infrared opacity of said sample at a selected thickness and at said selected frequency.

4. Apparatus for monitoring the crosslinker content of a room temperature vulcanizable silicone composition process stream comprising:
   (a) means for continuously bypassing a portion of said stream to a sample detection region, dividing said portion into first and second parts, and diverting said first part from said sample detection region;
   (b) a sample cell comprising a pair of opposed infrared transparent windows extending in parallel planes wherein the space between said windows is adjusted upon consideration of the relative viscosity of said room temperature vulcanizable silicone composition flowing in said process stream;
   (c) means for diverting said second part through said sample cell between said windows;
   (d) a laser effective for directing a beam of infrared radiation maintainable at a predetermined frequency corresponding to a selected infrared absorption frequency of the crosslinking agent contained in said process stream and at a power intensity effective to overcome the characteristic infrared opacity of said second part of said stream when filling the space between said windows, through said windows of said sample cell and through said second part of the RTV process stream flowing therebetween; and
   (e) means for continuously detecting the proportion of said infrared radiation when said radiation is absorbed by said second part of said sample cell at said predetermined frequency at said effective intensity.

5. Apparatus as in claim 4, wherein said infrared transparent windows are spaced from approximately 0.018 inches to approximately 0.024 inches apart.

6. Apparatus as in claim 4, wherein the constituent to be analyzed is a crosslinking agent for a room temperature vulcanizable silicone composition exhibiting crosslinking functionality of the type selected from the class of silanes and silioxanes consisting of alkoxy functional, acyloxy functional, acetoxy functional, amine functional, amide functional, and ketoximino functional silanes and siloxanes.

7. Apparatus as in claim 4, wherein the room temperature vulcanizable silicone composition in the process stream exhibits a viscosity of approximately 300,000 centipoise at 25° C. and the constituent to be monitored is a methyltriacetoxy silane crosslinker and wherein the opposed infrared transparent windows are spaced at least 0.018 to 0.024 inches apart and the infrared radiation is maintained at a frequency of approximately in the range of 1775 to 1800 cm$^{-1}$ and at a power intensity of at least ten milliwatts.

8. Apparatus as in claim 4, 5, 6 or 7, further comprising means for monitoring the flow rate of said second part of said stream flowing through said sample cell.

9. Apparatus for continuous analysis and control of a manufacturing process comprising:
   (a) means for individually containing a plurality of predetermined starting materials;
   (b) means for regulating the flow of said starting materials into a processor;
   (c) a conduit for directing a process stream from said processor to a receptacle;
   (d) means for diverting a sample of said process stream to a sample detection region;
   (e) means for irradiating said sample with infrared radiation directed through said detection region, wherein said radiation is adjusted to a frequency of infrared absorption corresponding to a characteristic absorption frequency of one of said starting materials, and wherein the power intensity of the radiation is sufficient to overcome the characteristic infrared opacity of said sample at a selected thickness and frequency;
   (f) a detector for determining infrared radiation absorbed by said sample;
   (g) means for detecting a continuous flow of said sample through said sample detection region and indicating any deviation from a predetermined flow rate through said region; and
   (h) a programmable means effective for interpreting absorption data, continuously storing said data, operating a trend recorder and controlling said means for regulating the flow of said starting materials.

10. Apparatus as in claim 9, wherein the process to be analyzed and controlled is a room temperature vulcanizable silicone manufacturing process exhibiting crosslinking functionality of the type selected from the class of silanes and siloxanes consisting of alkoxy functional, acyloxy functional, acetoxy functional, amine functional, amide functional, and ketoximino functional silanes and siloxanes.

11. Apparatus as in claim 10, wherein the room temperature vulcanizable silicone composition in the process stream exhibits a viscosity of approximately 300,000 centipoise at 25° C. and the constituent to be monitored is a methyltriacetoxy silane crosslinker and wherein the opposed infrared transparent windows are spaced approximately 0.018 to 0.024 inches apart and the radiation is maintained at a frequency of approximately 1775–1800 cm$^{-1}$ and at a power intensity of at least ten milliwatts.

12. A method for determining the concentration of a constituent in a process stream comprising the steps of:
   (a) bypassing a portion of said stream to a sample detection region;
   (b) splitting said portion of said stream into first and second parts and diverting said first part from the sample detection region;
   (c) diverting said second part of said stream through a sample region at a continuous thickness of approximately 0.010 inches to approximately 0.030 inches apart, said thickness being adjusted upon consideration of the relative viscosity of the stream flowing through said sample region;
   (d) directing a beam of infrared radiation maintainable at a predetermined frequency corresponding to a selected infrared absorption frequency of the constituent in the process stream under consideration, through said sample region and through said second part of the process stream flowing therethrough; and
   (e) continuously detecting the proportion of said infrared radiation at said predetermined frequency absorbed by said second part of said stream in said sample region.

13. A method as in claim 12, wherein the infrared radiation is maintained at a power intensity effective to overcome the characteristic infrared opacity of said sample at said frequency and sample thickness.

14. A method as in claim 13, wherein the process stream is a room temperature vulcanizable silicone and the constituent under consideration is a methyltriacetoxysilane crosslinker and wherein said infrared transparent windows of said sample cell are adjusted upon consideration of the relative viscosity of the process stream from approximately 0.018 inches to approximately 0.024 inches apart and said infrared radiation is selectively maintainable at a predetermined frequency corresponding to a selected infrared absorption frequency of methyltriacetoxysilane and at a power intensity effective to overcome the characteristic infrared opacity of said RTV process stream at said sample thickness and said selected absorption frequency.

15. A method as in claim 14, wherein the opposed infrared transparent windows are spaced approximately 0.018 to 0.024 inches apart and the infrared radiation is maintained at a frequency of about 1775–1800 cm$^{-1}$ and a power intensity of about at least ten milliwatts.

16. A method as in claim 15, further comprising the step of monitoring the flow rate of said sample stream.

17. A method as in claim 13, wherein the process stream is a room temperature vulcanizable silicone composition and wherein the concentration to be determined is of a constituent crosslinking agent exhibiting crosslinking functionality of the type selected from the class of silanes and siloxanes consisting of alkoxy functional, acyloxy functional, acetoxy functional, amine functional, amide functional, and ketoximino functional silanes and siloxanes.

* * * * *